| United States Patent [19] | [11] Patent Number: 4,764,510 |
| Hamill et al. | [45] Date of Patent: Aug. 16, 1988 |

[54] ANTIBIOTIC A42125 AND PROCESS FOR ITS PRODUCTION

[75] Inventors: Robert L. Hamill, Greenwood; Ralph E. Kastner, Indianapolis, both of Ind.

[73] Assignee: Eli Lilly and Company, Indianapolis, Ind.

[21] Appl. No.: 850,786

[22] Filed: Apr. 11, 1986

[51] Int. Cl.$^4$ .................. A61K 35/74; C12P 1/04
[52] U.S. Cl. .................................. 424/120; 435/170
[58] Field of Search ...................... 424/120; 435/170

[56] References Cited

U.S. PATENT DOCUMENTS 4,524,145 6/1985 Matson ................................. 514/43
4,552,842 11/1985 Nettleton et al. .................... 435/75

OTHER PUBLICATIONS

ATCC Catalogue of Bacteria, Phages, rDNA Vectors, 16th ed., 1985, p. 121.

Primary Examiner—Jerome D. Goldberg
Attorney, Agent, or Firm—Nancy J. Harrison; Leroy Whitaker

[57] ABSTRACT

Antibiotic A42125, which is produced by a new strain of *Nocardia aerocolonigenes*, NRRL 18049, is a useful inhibitor of Gram-positive and methane-generating microorganisms. A42125 also increases feed utilization efficiency in ruminants. A biologically purified culture of *N. aerocolonigenes* NRRL 18049 and a method for producing A42125 by fermentation of this culture are provided.

7 Claims, 1 Drawing Sheet

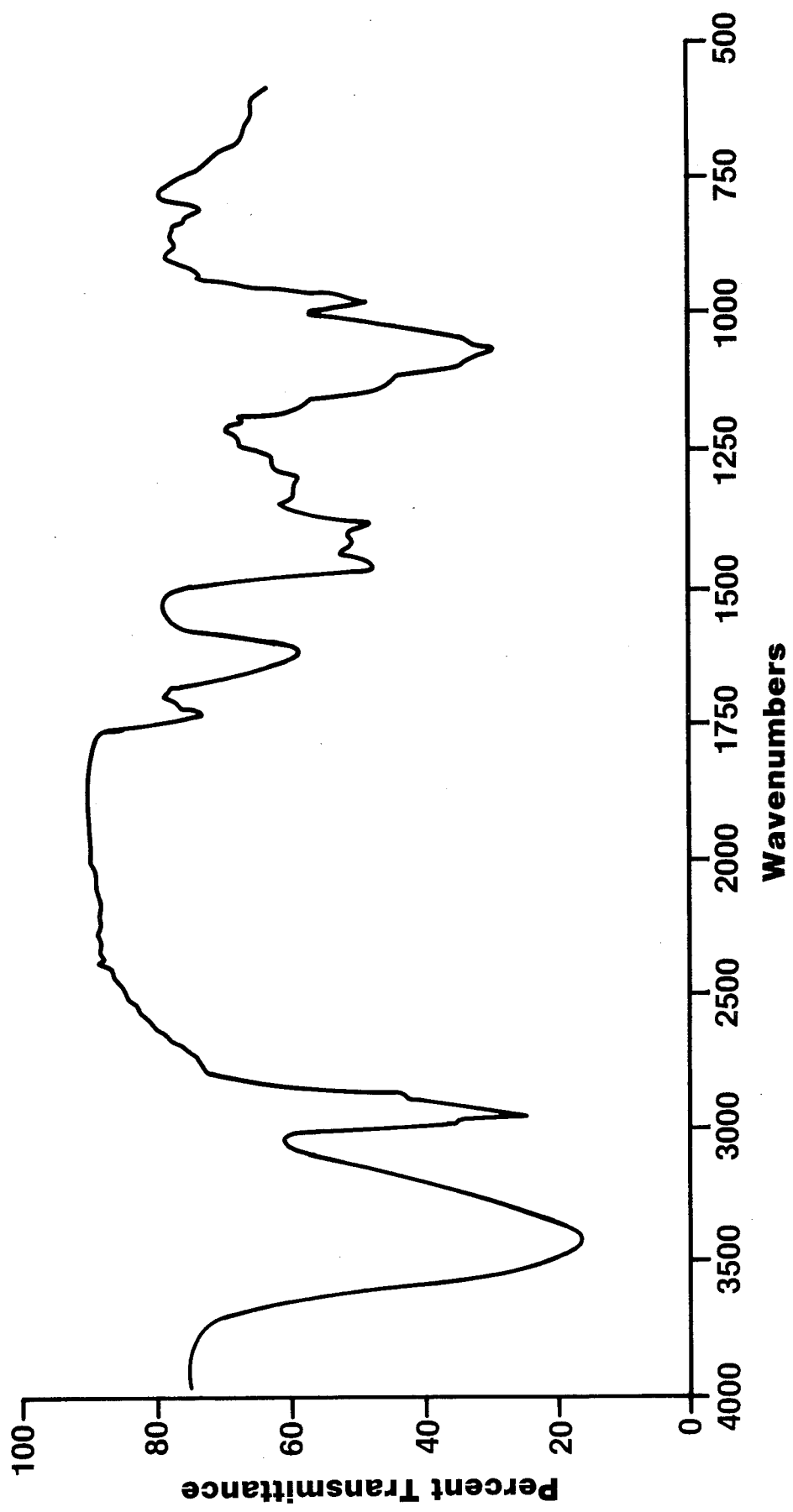

ANTIBIOTIC A42125 AND PROCESS FOR ITS PRODUCTION

SUMMARY OF THE INVENTION

This invention relates to a new antibiotic, A42125, and to a new strain of *Nocardia aerocolonigenes*, NRRL 18049, which produces this antibiotic. A42125 is an antibacterial agent which has particularly interesting activity against microorganisms which produce methane. Since A42125 minimizes methane production in tests simulating rumen conditions, A42125 should increase feed efficiency and, in turn, promote growth in ruminants.

Another aspect of this invention is the method of producing A42125 by culturing a new strain of *Nocardia aerocolonigenes*, NRRL 18049, under submerged aerobic fermentation conditions until a substantial level of the antibiotic is produced. A42125 is extracted from the fermentation broth by adsorbing it onto a resin and eluting the resin with a polar organic solvent. A42125 is separated and further purified by recognized techniques, such as ion exchange chromatography.

Because *Nocardia aerocolonigenes* NRRL 18049 is a newly discovered strain, this invention further relates to a biologically purified culture of this microorganism.

DESCRIPTION OF THE DRAWING

The accompanying drawing shows the infrared absorption spectrum of A42125 in KBr.

DETAILED DESCRIPTION OF THE INVENTION

There is a continuing need for improved antibiotics in the veterinary field. Promoting growth in animals is one goal for such antibiotics. Growth promotion is achieved by reducing disease and by increasing feed-utilization efficiency. Growth promotion in ruminants, such as cattle and sheep, is of particular commercial interest.

In ruminant animals, microorganisms in the rumen of the animal degrade carbohydrates to produce compounds which can be metabolized, such as propionates. Certain microorganisms, however, adversely affect the efficiency of this system. For example, methanogens or methane-producing microorganisms reduce the efficiency of feed utilization in ruminants. A special advantage of A42125 is that it inhibits methane-generating microorganisms and, therefore, can be used to promote growth in ruminants.

Although they are undesirable in the ruminant digestive system, methane-generating microorganisms (archaebacteria) are important contributors to the world's environment because they catalyze the final stage in which waste biomass is decomposed to methane. Furthermore, methane may become useful as a fuel, thereby helping to solve energy resource problems. Thus, methanogens and methods for increasing methane generation are important.

One approach to increasing methane production is to develop genetic exchange systems in methanogens. In order to accomplish this, selectable traits, such as antibiotic resistance, are essential. Such traits are usually found by selecting mutants which are resistant to an antibiotic which normally kills the microorganism. Unfortunately, methanogens are naturally resistant to most antibiotics. Thus, the fact that A42125 inhibits methanogens should make it useful for locating a selectable trait to facilitate genetic exchange in methanogens.

Characteristics of A42125

Antibiotic A42125 has the following physiochemical characteristics:

State: White crystals (from water).
mp: 149°–150° C.
UV: No absorption.
IR (Kbr): See the accompanying drawing; shows absorption at the following frequencies (cm$^{-1}$): broad peak which includes 3423, 3413, 3409, 3403, 3398 and 3386; 2937, 1720, 1602, 1453, 1408, 1379, 1290, 1192, 1120, 1090, 1064, 971, 870, 830 and 802.
Titration (80% aqueous dimethylformamide): pKa's 5.2, 8.7 and 10.5
Molecular weight: 2032 (field desorption mass spectrometry).
Empirical formula: $C_{101}H_{184}N_2O_{38}$.
Elemental analysis:

| Element | Found % |
| --- | --- |
| Carbon | 59.51 |
| Hydrogen | 9.05 |
| Nitrogen | 1.44 |
| Oxygen | 30.08 |

Amino acids: None found.
Solubility: Soluble in water.
Bioautography: Using Whatman No. 1 paper impregnated with 0.95N $Na_2SO_4$ and 0.05 $NaHSO_4 \cdot H_2O$, a solvent system of 80% aqueous ethanol containing 1.5% NaCl and detecting with *Micrococcus luteus*, A42125 had an Rf value of approximately 0.46.

Based on its titration characteristics, it appears that A42125 may have a carboxyl group, an amine function and a phenolic group which could form salts.

Such salts would be useful for separating, purifying and delivering the antibiotic. A42125 salts are, therefore, part of this invention. The pharmaceutically acceptable salts are particularly useful. Examples of useful salts are the alkali-metal, alkaline-earth-metal amine and acid addition salts.

Representative and suitable alkali-metal and alkaline-earth metal salts include the sodium, potassium, lithium, cesium, rubidium, barium, calcium and magnesium salts. Suitable amine salts include the ammonium and the primary, secondary, and tertiary $C_1$–$C_4$-alkylammonium and hydroxy-$C_2$–$C_4$-alkylammonium salts. Illustrative amine salts include those formed by reaction of A42125 with ammonium hydroxide, methylamine, sec-butylamine, isopropylamine, diethylamine, di-isopropylamine, ethanolamine, triethylamine, 3-amino-1-propanol, and the like.

Representative acid addition salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

In the veterinary pharmaceutical art, the form of an antibiotic is not ordinarily of great significance when treating an animal with the antibiotic. In most cases, conditions within the animal change the drug to a form other than that in which it was administered. The salt form in which it may be administered is, therefore, not generally of great importance. The salt form may, however, be chosen for reasons of economy, convenience, and toxicity.

Antibiotic A42125 is produced by culturing an A42125-producing strain of *Nocardia aerocolonigenes* under submerged aerobic conditions in a suitable culture medium until substantial antibiotic activity is produced. A42125 can be recovered using various isolation and purification procedures understood in the art.

The new *Nocardia aerocolonigenes* strain which is useful for the preparation of antibiotic A42125 was isolated from a soil sample from Brazil. For convenience in describing the *N. aerocolonigenes* strain, it is called the A42125 culture.

Taxonomic studies of this organism were carried out by Frederick P. Mertz of the Lilly Research Laboratories. Based on these studies, the organism is classified as a new strain of *Nocardia aerocolonigenes* (Shinobu and Kawato) Pridham and Lyons 1970 (T. G. Pridham, "New Names and New Combinations in the Order Actinomycetales Buchanan 1917," USDA Tech. Bull. No. 1424:32, Agricultural Research Service, USDA, Washington, D.C., 1970). This classification is based on simultaneous laboratory comparisons, as well as an examination of published descriptions of similar species [M. Goodfellow and K. P. Schaal, "Identification Methods for Nocardia, Actinomadura and Rhodococcus," in F. A. Skinner and D. W. Lovelock, ed., "Identification Methods for Microbiologists," 2nd ed., Society for Applied Bacteriology Technical Series No. 14, Academic Press Inc., New York, 1979, p. 261; R. E. Gordon, S. K. Mishra and D. A. Barnett, "Some Bits and Pieces of the Genus *Nocardia: N. carnea, N. vaccinii, N. transvalensis, N. orientalis,* and *N. aerocolonigenes,*" *J. Gen. Microbiol.* 109, 69–78 (1978); S. J. Mishra, R. E. Gordon, and D. A. Barnett, "Identification of Nocardiae and Streptomycetes of Medical Importance," *J. Clin. Microbiol.* 11(6), 728–736 (1980); H. Mordarska and M. Mordarski, "Chemotaxonomic Characters and Classification of Some Nocardioform Bacteria," *J. Gen. Microbiology* 71; 77–86 (1972); R. C. Pittenger and R. B. Brigham, "*Streptomyces orientalis,* n.sp., the Source of Vancomycin," *Antibiotics and Chemotherapy* VI(11); 642–647 (1956); and S. A. Waksman, "The Actinomycetes, Vol. II", The Williams and Wilkins Co., Baltimore, 1961].

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)]have been followed along with certain supplementary tests (D. J. Blazevic and G. M. Ederer, "Principles of Biochemical Tests in Diagnostic Microbiology", John Wiley and Sons, Inc., New York, 1975).

Methods recommended for the characterization of Nocardia species by Gordon et. al. [R. E. Gordon, D. A. Barnett, J. E. Handerhan, and C. H. Pang, "*Nocardia coeliaca, Nocardia autotrophica,* and the *Nocardin Strain,*" *Int. J. Syst. Bacteriol.* 24(1), 54–63 (1974)]have been followed.

Resistance to rifampin and lysozyme was measured by methods recommended by Gordon and Barnett [R. E. Gordon and D. A. Barnett, "Resistance to Rifampin and Lysozyme of Strains of Some Species of Mycobacterium and Nocardia as a Taxonomic Tool," *Int. J. Syst. Bacteriol.* 27(3), 176–178 (1977)].

ICSS-NBS Centroid Color Charts, standard sample No. 2106 (National Bureau of Standards, 1958, U.S. Department of Commerce, Washington, D.C.) and the Color Harmony Manual (4th ed., Color Standards Department, Container Corporation of America, Chicago, Ill., 1958) were used to assign color names.

Morphology was studied using an optical light microscope. A scanning electron microscope (SEM) was used to study the spore surface ornamentation.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 which has tyrosine removed.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates", *Appl. Microbiol.* 12, 421–423 (1964)]and of Lechevalier [M. P. Lechevalier, "Identification of Aerobic Actinomycetes of Clinical Importance," *J. Lab. Clin. Med.* 71, 934–944 (1968)].

Mycolic acids were determined by a method based on techniques described by Minnikin [D. E. Minnikin, I. G. Hutchinson and A. B. Caldicott, "Thin-layer Chromatography of Methanolysates of Mycolic Acid-containing Bacteria," *J. Chromatography* 188; 221–233 (1980)].

Starch hydrolysis was determined by testing for the presence of starch with iodine on ISP No. 4 (inorganic salts-starch agar) plates (see Blazevic and Ederer, supra).

NaCl tolerance was measured by adding NaCl to ISP No. 2 agar to equal the concentration desired and incubating the plates at 30° for 14 days.

Resistance to antibiotics was measured by padding antibiotic sensitivity discs onto the surface of seeded ISP No. 2 agar plates.

Phosphatase and urease were determined by methods described by Blazevic and Ederer, supra. Gelatin liquefaction was used to determine proteinase activity.

Cultural Characteristics

Growth of A42125 was generally good on both complex and defined agar media. Aerial mycelia were produced on all but yeast-dextrose agar. The spore mass color was in the gray-to-white color series. The nearest matching color tabs in the Tresner and Bachus system were d light gray and b oyster white. The reverse side color was yellowish brown to yellowish white. A light brown soluble pigment was produced in ISP No. 2 and yeast-dextrose agar. Table I summarizes these cultural characteristics.

TABLE I

Cultural Characteristics of A42125, *N. aerocolonigenes*, and *N. orientalis*

| Medium | Characteristic[a] | A42125 | *N. orientalis* | *N. aerocolonigenes* |
|---|---|---|---|---|
| ISP 2 | G: | Abundant | Abundant | Abundant |
| | R: | 78.d.yBR | 68.s.OY | 72.d.OY |
| | Am: | Abundant: 5fe 1.gy.rBn | Abundant: 2ba Pale yellow | None (wrinkled surface) |
| | Sp: | Light-brown | None | None |
| ISP 3 | G: | Good | Good | Fair |
| | R: | 89.p.Y | 89.p.Y | 89.p.Y |
| | Am: | Fair: b Oyster white | Good: b Oyster white | None |
| | Sp: | None | None | None |
| ISP 4 | G: | Good | Abundant | Good |
| | R: | 77.m.yBr | 72.d.OY | 90.gy.Y |
| | Am: | Good: d Light gray | Abundant: d Light gray | None: |
| | Sp: | None | None | None |
| ISP 5 | G: | Abundant | Abundant | Abundant |
| | R: | 77.m.yBr | 67.brill.OY | 88.d.Y |
| | Am: | Abundant: b Oyster white | Abundant: 2ba Pale yellow | None (wrinkled surface) |
| | Sp: | None | None | None |
| Calcium Malate | G: | Good | Abundant | Good |
| | R: | 77.m.yBr | 67.brill.OY | 88.d.Y |
| | Am: | Good: b Oyster white | Abundant: 2ba Pale yellow | None |
| | Sp: | None | None | None |
| Czapek's Solution Agar | G: | Good | Good | Abundant |
| | R: | 77.m.yBr | 89.p.Y | 75.deep yBr |
| | Am: | Good: d Light gray | Good: b Oyster white | None (wrinkled surface) |
| | Sp: | Very light brown | None | Light yellow-brown |
| Glucose-Asparagine | G: | Good | Abundant | Good |
| | R: | 89.p.Y | 67.brill.OY | 88.d.Y |
| | Am: | Poor: d Light gray | Abundant: 2ba Pale yellow | None |
| | Sp: | None | None | None |
| Tap Water Agar | G: | Good | Fair | Poor |
| | R: | 92.y White | 93.yGray | 92.yWhite |
| | Am: | Fair: b Oyster white | Poor: b Osyter white | None |
| | Sp: | None | None | None |
| Yeast-Dextrose Agar | G: | Abundant | Abundant | Abundant |
| | R: | 78.d.yBr | 68.s.OY | 72.d.OY |
| | Am: | None (wrinkled surface) | Abundant: 2ba Pale yellow | None: (wrinkled surface) |
| | Sp: | Light brown | None | None |

[a] G = growth;
R = reverse;
Am = aerial mycelium;
Sp = soluble pigment.

Morphological characteristics

Culture A42125 produced an extensive substrate and fairly well developed aerial mycelium. When viewed under a light microscope, the aerial hyphae have a cobweb appearance. This morphology is classified in the non-streptomycetes section described in Bergey's Manual (R. E. Buchanan, and N. E. Gibbons Eds., "Bergey's Manual of Determinative Bacteriology," 8th ed., The Williams and Wilkins Co., Baltimore, 1974).

Conidia were observed when aerial hyphae from ISP No. 4 agar medium were examined by scanning electron microscopy.

Spores were poorly and irregularly formed. The spore surface ornamentation was smooth [(T. G. Pridham, C. W. Hesseltine, and R. C. Benedict, "A Guide for the Classification of Streptomycetes According to Selected Groups," *Appl. Microbiol.* 6; 52–79 (1957)].

The spore shape was oblong to cylindrical and formed chains of greater than 50 in number. The spore size ranged from 1.2–0.9 ×0.5–0.4 μM, and averaged 1.1×0.5 μM.

When grown under submerged shaken conditions, the hyphae separated into fragments.

Physiological characteristics

Culture A42125 decomposed casein, elastin, guanine, hypoxanthine and tyrosine; hydrolyzed calcium malate, DNA, esculin and starch; formed acid from arabinose, cellobiose, fructose, galactose, α-methyl-D-glycoside, glucose, glycerol, inositol, lactose, maltose, mannitol, mannose, melibiose, raffinose, rhamnose, trehalose and xylose; utilized acetate, benzoate, citrate, malate, oxalate, propionate, pyruvate, succinate and tartrate.

Culture A42125 produced catalase, phosphatase, proteinase, urease and melanoid pigments; was not resistant to rifampin; but was resistant to lysozyme, cephalothin, gentamicin, lincomycin, penicillin and tobramycin.

Culture A42125 tolerated up to 6% NaCl and grew at temperatures between 15°–37° C.; it was unable to survive exposure to 50° C. for 8 hours, hydrolyze skim milk or reduce nitrates to nitrites. These physiological properties are shown in Tables II and III.

TABLE II

Some Morphological and Physiological Properties of A42125 and Related Nocardia Strains[a]

| Property | A42125 | N. aero-colonigenes | N. orientalis | N. brasiliensis |
|---|---|---|---|---|
| Aerial hyphae | + | − | − | − |
| Conidia | + | − | + | − |
| Acid fastness | − | − | − | − |
| Mycolic acids in cell walls | − | − | − | + |
| Urease | + | + | + | + |
| *Decomposes:* | | | | |
| Adenine | − | − | − | − |
| Casein | + | + | + | + |
| Elastin | + | − | − | + |
| Hypoxanthine | + | + | + | + |
| Tyrosine | + | + | + | + |
| Xanthine | − | − | − | − |
| *Resistance to:* | | | | |
| Lysozyme | + | + | − | + |
| Rifampin | − | − | + | + |
| *Hydrolyzes:* | | | | |
| Calcium malate | + | + | + | ND |
| Esculin | + | + | + | + |
| Hippurate | − | − | + | − |
| Starch | + | + | + | + |
| *Utilizes:* | | | | |
| Benzoate | + | − | − | − |
| Citrate | + | + | + | + |
| Mucate | − | − | − | − |
| Succinate | + | + | + | + |
| Tartrate | + | − | − | − |
| Reduces Nitrate | − | − | + | + |
| Survives at 50° C., 8 h | − | − | + | − |
| *Forms Acid from:* | | | | |
| Adonitol | − | − | + | − |
| 1-(+)-Arabinose | + | + | + | − |
| Cellobiose | + | + | + | + |
| i-Erythritol | − | − | + | − |
| Glucose | + | + | + | + |
| *Forms Acid from:* | | | | |
| Glycerol | + | + | + | + |
| Inositol | + | + | + | + |
| α-Lactose | + | + | + | − |
| Maltose | + | + | + | − |
| D-Mannitol | + | + | + | + |
| D-Mannose | + | + | + | + |
| Melezitose | − | − | − | − |
| Melibiose | + | + | − | − |
| α-Methylglucoside | + | − | + | − |
| Raffinose | + | + | − | − |
| Rhamnose | + | + | + | − |
| Sorbitol | − | − | − | − |
| Trehalose | + | + | + | + |
| Xylose | + | + | + | − |
| *Grows at:* | | | | |
| 10° | − | + | + | + |
| 45° | − | − | − | − |
| 50° | − | − | − | − |

[a] + = exhibits property; − = does not exhibit property

TABLE No. III

Additional Properties of A42125

| Property | Characteristic[a] |
|---|---|
| Phosphatase | + |
| Hydrolyzes skim milk | − |
| Melanoid pigment production | + |
| Gelatin liquefaction | + |
| NaCl tolerance % | 6 |
| Catalase | + |
| *Decomposes:* | |
| Chitin | − |
| DNA | + |
| Guanine | + |
| Keratin | − |
| Testosterone | − |
| *Utilizes:* | |
| Acetate | + |
| Malate | + |
| Oxalate | + |
| Propionate | + |
| Pyruvate | + |
| *Forms Acid from:* | |
| Dulcetol | − |
| Ethanol | − |
| Fructose | + |
| d-(+)-Galactose | + |
| Inulin | − |
| Salicin | − |
| Sucrose | − |
| Temperature range for growth | 15–37° C. |

[a] + = strain has property; − = strain does not have property

Cell-Wall Analysis

Hydrolyzed whole cells contained the meso isomer of diaminopimelic acid. Sugars present in whole cell hydrolysates were arabinose, galactose, mannose and ribose. The cell-wall type according to Becker, supra, was Type IV, and the sugar pattern was Type A (Lechevalier, supra). Mycolic acids (LCN-A) were not produced by A42125. The cells stained Gram positive but were not acid fast.

Identity of Strain A42125

Strain A42125 has a Type IV cell wall, Type A whole cell sugar pattern, and does not contain mycolic acids (LCN-A). This chemotaxonomic information and the general cultural characteristics are consistent with assignment of strain A42125 to the genus Nocardia Trevisan 1889 [V. B. D. Skerman, V. McGowan, and P. H. A. Sneath, Eds., "Approved Lists of Bacterial Names," *Int. J. Syst. Bacteriol.* 30; 225–420 (1980)].

Comparison of characteristics of strain A42125 to published descriptions of Nocardia species showed similarity to the following species:

Nocardia aerocolonigenes[a,b]
Nocardia brasiliensis[a,b]
Nocardia orientalis[a,b,c]

These cultures were grown simultaneously with strain A42125. Published data and experimental data were combined, and the results were evaluated.

[a] Goodfellow and Schaal, supra
[b] Gordon, Mishra and Barnett, supra
[c] Pittenger and Brigham, supra Similarity coefficients were calculated as discussed by Kurylowicz et al., (W. Kurylowicz, A. Paszkiewicz, W. Woznicka, W. Kurzatkowski and T. Szulga, "Numerical Taxonomy of Streptomycetes," Polish Medical Publishers, Warsaw, 1975, p. 37), using the following equation:

$$S_{SM} = \frac{Ns^+ + Ns^-}{Ns^+ + Ns^- + Nd} \times 100$$

where $Ns^+$ is the number of positive similarities, $Ns^-$ the number of negative similarities, and $Nd$ is the number of dissimilarities (differences).

The properties used to calculate the $S_{SM}$ were physiological and not cultural or morphological. The total number of properties equaled 44.

The similarity coefficients are given below:

| Culture | $S_{SM}$ |
|---|---|
| A42125 | 100 |
| N. aerocolonigenes | 88 |
| N. orientalis | 70 |
| N. brasiliensis | 65 |

Because *N. brasiliensis* had little resemblance culturally to A42125 and a low $S_{SM}$ value, it was eliminated from consideration.

*N. orientalis* had cultural characteristics similar to those of A42125. This similarity is especially apparent on ISP media Nos. 3 and 4. It was eliminated from consideration, however, because the physiological characteristics were not similar, as indicated by the low $S_{SM}$.

*N. aerocolonigenes* does not have aerial hyphae. Therefore, a cultural comparison to A42125 could be made only on the basis of growth, reverse color and soluble pigments. When *N. aerocolonigenes* was first described [E. B. Shirling, and D. Gottlieb, "Cooperative Description of Type Cultures of Streptomyces 111," *Int. J. Syst. Bacteriol.* 18(4); 279-392 (1968)], it was reported to have white aerial hyphae on ISP No. 5. This report agrees with observations from the current simultaneous comparison study (see Table I, ISP No. 5). The growth and reverse color of A42125 and *N. aerocolonigenes* match acceptably. This match is demonstrated especially well on Czapek's solution agar and glucose-asparagine agar.

Gordon, *supra*, classified strains as *N. aerocolonigenes*, using properties other than aerial hyphae. The physiological and chemotaxonomic similarities between A42125 and *N. aerocolonigenes* far outweighed the differences due to the absence of aerial hyphae. Three key properties were given by Gordon to distinguish *N. orientalis* from *N. aerocolonigenes*. A comparison of these properties with those of A42125 are listed in Table IV:

TABLE IV

Comparison of Distinguishing Properties of A42125, *N. orientalis* and *N. aerocolonigenes*

| Property[a] | N. orientalis | N. aerocolonigenes | A42125 |
|---|---|---|---|
| erythritol | + | − | − |
| α-methylglucoside | + | − | + |
| resistance to lysozyme | − | + | + |

[a] + = strain has property
− = strain does not have property

Inspection of these indicators shows that A42125 is most closely related to *N. aerocolonigenes*.

A42125 and *N. aerocolonigenes* differ in carbon utilization (measured by growth and acid production) by only one carbohydrate source.

Using the key devised by Mishra, supra, for the tentative identification of species of Nocardiae, culture A42125 keyed directly to *N. aerocolonigenes*. These comparisons indicate that A42125 has a limited cultural similarity and good physiological similarity to *N. aerocolonigenes*. The most significant difference is the presence of aerial hyphae in A42125. Since *N. aerocolonigenes* has been known to produce aerial hyphae, this difference is not considered sufficient to exclude A42125 from this taxon. Therefore, culture A42125 is classified as a strain of *Nocardia aerocolonigenes* (Shinobu and Kawato) Pridham and Lyons 1970. Because *N. aerocolonigenes* is not in the Approved Lists of Bacterial Names, supra, however, it is not a validly published species.

As is the case with other organisms, the characteristics of the A42125-producing culture, *Nocardia aerocolonigenes* NRRL 18049, are subject to variation. Recombinants, mutants or variants of the strain may be obtained by methods known in the art. For example, mutants can be obtained by treatment with various known physical and chemical mutagens such as ultraviolet light, X-rays, gamma rays and chemicals such as N-methyl-N'-nitro-N-nitrosoguanidine. All natural and induced variants, mutants and recombinants of *Nocardia aerocolonigenes* which retain the characteristic of A42125 production are part of this invention.

The culture medium used to grow *Nocardia aerocolonigenes* NRRL 18049 can be any one of a number of media. For economy in production, optimal yield, and ease of product isolation, however, certain culture media are preferred. For example, for *N. aerocolonigenes* preferred carbohydrate sources in large-scale fermentation are glucose and dextrins, although other sugars or sugar polymers and the like can also be used.

Preferred nitrogen sources for *N. aerocolonigenes* are soybean grits and corn-steep liquor, although other nitrogen sources such as distillers solubles, yeast extract, beef extract, and the like can also be used.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 mL/L) of an antifoam agent such as polypropylene glycol may be added to large scale fermentation media if needed.

For production of substantial quantities of antibiotic A42125, submerged aerobic fermentation in tanks is preferred. Small quantities of A42125 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A42125 is produced by *Nocardia aerocolonigenes* when grown at temperatures between about 25° and about 37° C. A good temperature for A42125 production appears to be about 30° C.

As is customary in submerged aerobic culture processes, sterile air is blown into the vessel from the bottom while the medium is stirred with conventional turbine impellors. Under the conditions used thus far, the maximum oxygen uptake of the fermentation does not exceed about 0.2 mM/L/minute. In a fully baffled 165 liter fermentor containing approximately 115 liters of broth, an aeration rate of 0.125 v/v/m with an agitation rate of 200–250 rpm is sufficient to maintain the level of dissolved oxygen at or above 30% of air saturation.

Production of antibiotic A42125 can be followed during the fermentation by testing samples of the broth for antibiotic activity against organisms known to be sensitive to the antibiotic. One assay organism useful in testing for the presence of A42125 is *Micrococcus luteus*. The bioassay is conveniently performed by the agar-well plate test.

Following its production under submerged aerobic fermentation conditions, A42125 can be recovered from the fermentation medium by methods used in the fermentation art. The antibiotic activity produced during fermentation of the A42125-producing organism occurs mainly in the broth. Maximum recovery of A42125 is accomplished, therefore, by initially filtering the medium to separate the broth from the mycelial mass. The filtered broth can then be purified to separate the A42125. A variety of techniques may be used in this purification.

A preferred technique for separating A42125 from the filtered broth involves adjusting the broth to a pH of about 7 and adding a suitable adsorbent such as, for example, Diaion HP-20 resin. The resin is separated filtration and extracted with a suitable solvent such as acetonitrile:water (1:1). The extracting solvent can then be evaporated under vacuum to give A42125.

The A42125 obtained in this manner can be further purified by recognized procedures. A preferred procedure involves ion exchange chromatography.

Separation of antibiotic A42125 can be followed by thin-layer chromatography (TLC). One convenient silica-gel TLC solvent system is acetonitrile: methanol:water:ammonium hydroxide (4:2:2:1). In this system A42125 has an Rf value of approximately 0.43. The antibiotic can be detected by bioautography using, for example, *Micrococcus luteus* or by other methods such as, for example, vanillin-sulfuric acid spray reagent.

Alternatively, the culture solids, including medium constituents and mycelium can be used without extraction or separation, but preferably after removal of water, as a source of A42125. For example, after production of A42125, the whole fermentation broth can be dried by lyophilization, by drum-drying, or by azeotropic distillation and drying. The dried broth is then mixed directly into feed premix.

A42125 inhibits the growth of bacteria which are pathogenic to animal and plant life. Table V summarizes the minimal inhibitory concentrations (MIC's) at which A42125 inhibits various bacteria, as measured by the conventional agar-dilution method.

TABLE V

Antibacterial Activity of A42125

| Test Organism | MIC (mcg/mL) |
| --- | --- |
| *Staphylococcus aureus* V1.1 | 1 |
| *Staphylococcus aureus* V41 | 1 |
| *Staphylococcus aureus* X400 | 1 |
| *Staphylococcus aureus* S13E | 1 |
| *Staphylococcus epidermidis* Epi 1 | 1 |
| *Staphylococcus epidermidis* 222 | 0.5 |
| *Streptococcus pyogenes* C203 | 2 |
| Streptococcus sp. group D X66 | 1 |
| Streptococcus sp. group D 2041 | 4 |
| *Haemophilus influenzae* 76 | 8 |

One important aspect of the antimicrobial activity of A42125 relates to its activity against anaerobic bacteria. MIC's at which A42125 inhibits various anaerobic bacteria, as determined by standard agar-dilution assay, are summarized in Table VI. End points were read after 24-hour incubation.

TABLE VI

Susceptibility of Anaerobic Bacterial Isolates to A42125

| Anaerobic Bacteria | MIC (mcg/mL) |
| --- | --- |
| *Clostridium difficile* 2994 | 4 |
| *Clostridium perfringens* 81 | 4 |
| *Clostridium septicum* 1128 | 4 |
| *Eubacterium aerofaciens* 1235 | 4 |
| *Peptococcus asaccharolyticus* 1302 | 64 |
| *Peptococcus prevoti* 1281 | 4 |
| *Peptostreptococcus anaerobius* 1428 | 8 |
| *Peptostreptococcus intermedius* 1624 | 4 |
| *Propionibacterium acnes* 79 | 8 |
| *Bacteroides fragilis* 111 | >128 |
| *Bacteroides fragilis* 1877 | >128 |
| *Bacteroides fragilis* 1936B | >128 |
| *Bacteroides thetaiotaomicron* 1438 | 128 |
| *Bacteroides melaninogenicus* 1856/28 | 64 |
| *Bacteroides melaninogenicus* 2736 | 128 |
| *Bacteroides vulgatis* 1211 | 128 |
| *Bacteroides corrodens* 1874 | >128 |
| *Fusobacterium symbiosum* 1470 | >128 |
| *Fusobacterium necrophorum* 6054A | ≧0.5 |

In another important aspect of its antimicrobial activity, A42125 inhibits methane-generating bacteria. For example, A42125 inhibited *Methanococcus vannielli* in concentrations as low as 0.1 mcg/mL in a test in which one crystal of A42125 was placed on a 24-hour lawn (minimal medium) and inhibition was measured at 3 days.

Another important property of A42125 is its ability to improve feed-utilization efficiency in animals. For example, A42125 improves feed-utilization efficiency in ruminants which have a developed rumen function.

The efficiency of feed use can be monitored by observing the production and concentration of propionate compounds in the rumen, using the method described by Arthur P. Raun in U.S. Pat. No. 3,794,732 (see especially Example 5). Table VII shows the ratios of volatile-fatty-acid (VFA) concentrations in A42125-treated flasks to concentrations in control flasks in these tests.

TABLE VII

Effect of A42125 on Ruminant Feed-Utilization Efficiency[a]

| Dosage mcg/mL | Molar % Propionate | Molar % Acetate | Molar % Butyrate | Total VFA/ Control VFA mM/L |
| --- | --- | --- | --- | --- |
| 20 | 1.283 | 0.914 | 0.608 | 0.921 |
| 5 | 1.237 | 0.877 | 1.019 | 0.988 |
| 5 | 0.959 | 0.992 | 1.075 | 0.921 |
| 1 | 1.122 | 1.015 | 0.795 | 1.237 |
| 5 | 1.118 | 0.915 | 0.867 | 1.041 |
| 1 | 1.105 | 0.881 | 1.111 | 0.997 |
| 5 | 1.778 | 0.896 | 0.654 | 0.921 |
| 1 | 1.458 | 0.915 | 0.823 | 0.858 |

[a]Five tests

Methane inhibition also contributes to more efficient feed utilization in ruminants by diverting the acetate to usable energy instead of methane, which is expelled. This activity can be measured using an in vitro test which mimics the action of the rumen. The test method was described by James R. Beck and Joseph A. Yahner in U.S. Pat. No. 4,333,923 (see columns 6–7). Table VIII summarizes the methane-inhibiting activity of A42125 when measured by the method of Beck et al.

TABLE VIII

Effect of A42125 on Ruminant Methane Production[a]

| Dosage mcg/mL | Methane mM/day |
|---|---|
| — | 23.0 |
| 5 | 2.3 |
| — | 4.1 |
| 5 | 1.8 |
| 1 | 2.3 |
| — | 7.2 |
| 5 | 0.3 |
| 1 | 0.8 |

[a]Three tests

Estimated LD50's after single-dose administration of A42125 in mice are:

LD50 (intraperitoneal) = <9.375 mg/kg
LD50 (oral) = 89 mg/kg

A42125 is typically effective in increasing propionates and, thereby, the efficiency of feed utilization when administered to ruminants orally at rates of from about 0.05 mg/kg/day to about 6.75 mg/kg/day. Preferable rates of administration are from about 2 mg/kg/day to about 3.5 mg/kg/day.

A preferred method of administration is to mix the compound with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of a compound of this invention directly related to the proper daily dose for the animal to be treated.

This invention further relates to feed compositions adapted to increase feed utilization comprising feed ration and from 6 to 60 grams per ton of A42125 compound.

A42125 can be administered to animals orally or parenterally. The most practical way to administer A42125 is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses or capsules. Each individual dosage unit should contain a quantity of A42125 directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals will depend upon the amount of drug to be administered. The common methods of formulating, mixing and pelleting feeds may be used to prepare feeds containing A42125.

A42125 may be formulated for parenteral administration by methods recognized in the veterinary pharmaceutical art. Effective injectable compositions containing A42125 may be in either suspension or solution form. In the solution form, A42125 is dissolved in a physiologically acceptable carrier. Such carriers comprise a suitable solvent, preservatives such as benzyl alcohol, if needed, and buffers. Useful solvents include, for example, water, alcohols, glycols or inert oils such as vegetable oils or highly refined mineral oils.

Injectable suspension compositions are prepared using a nonsolvent for the compound with adjuvants as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin and the alginates. Many surfactants are also useful for suspending the compounds. Lecithin, alkylphenol polyethylene oxide adducts, naphthalenesulfonates, alkylbenzenesulfonates and the polyoxyethylene sorbitan esters are useful suspending agents in liquid nonsolvents.

Many substances which affect the hydrophilicity, density and surface tension of the liquid nonsolvent can assist in making injectable suspensions in individual cases. For example, silicone antifoams, glycols, sorbitol and sugars can be useful suspending agents.

In order to illustrate more fully the operation of this invention, the following examples are provided:

EXAMPLE 1

Preparation of Antibiotic A42125

A. Shake-flask Fermentation

The culture *Nocardia aerocolonigenes* NRRL 18049, either as a lyophilized pellet or as a suspension maintained in liquid nitrogen, is used to inoculate a slant medium having the following composition:

| Slant Medium | |
|---|---|
| Ingredient | Amount (g/L) |
| Potato Dextrin | 10 |
| Yeast Extract | 1 |
| Enzyme-hydrolyzed Casein* | 2 |
| Beef Extract | 1 |
| $COCl_2.6H_2O$ | 0.01 |
| Agar | 20 |
| Deionized Water | q.s. 1 liter |

*N-Z Amine A, Humko Sheffield Chemical Co., Lyndhurst NJ
pH is adjusted from ~6.2 to 7.0 with NaOH The inoculated slant is incubated at 30° C. for from about 7 days. The mature slant culture is scraped with a sterile tool to loosen the spores and remove and macerate the mycelial mat. About one-fourth of the loosened spores and culture growth thus obtained is used to inoculate 50 mL of a vegetative medium having the following composition:

| Vegetative Medium | |
|---|---|
| Ingredient | Amount (g/L) |
| Glucose | 15 |
| Tapioca Dextrin* | 20 |
| Soybean Grits | 15 |
| Corn Steep Liquor | 10 |
| Yeast Extract | 1 |
| $CaCO_3$ | 2 |
| Tap Water | q.s. to 1 liter |

*Stadex 11, A. E. Staley Co., Decatur IL
pH adjusted from ~5.5 to 6.5 with NaOH

The inoculated vegetative medium is incubated in a 250-mL Erlenmeyer flask at 30° C. for about 72 hours on a shaker orbiting in a two-inch (5.08 cm) circle at 250 rpm.

This incubated vegetative medium (1.25 mL) is used to inoculate 50 mL of a production medium having the following composition:

| Ingredient | Amount (g/L) |
| --- | --- |
| Glucose | 25 |
| Corn Starch | 10 |
| Soluble Meat Peptone* | 10 |
| Enzyme-hydrolyzed Casein** | 4 |
| Blackstrap Molasses | 5 |
| $MgSO_4.7H_2O$ | 0.5 |
| $CaCO_3$ | 2.0 |
| Czapek's Mineral Stock*** | 2 mL |
| Deionized Water | q.s. 1 liter |

*O. M. Peptone, Amber Laboratories, Juneau WI
**N-Z Amine A
***Czapek's mineral stock has the following composition: 100 g KCl; 100 g $MgSO_4.7H_2O$; 2 g $FeSO_4.7H_2O$; q.s. to 1 liter with deionized water The inoculated production medium is incubated in a 250-mL wide-mouth Erlenmeyer flask at 30° C. for 3 to 5 days on a shaker orbiting in a two-inch circle at 250 rpm.

B. Tank Fermentation

In order to provide a large volume of inoculum, 10 mL of incubated vegetative medium, prepared as described in Section A, is used to inoculate 250 mL of a second-stage growth medium having the same composition as that of the vegetative medium. This second-stage medium is incubated in a two-liter wide-mouth Erlenmeyer flask for about 70 hours at 30° C. on a shaker orbiting in a two-inch circle at 250 rpm.

Incubated second-stage medium (400 mL) thus prepared is used to inoculate 100 liters of sterile production medium, prepared as described in Section A. The inoculated production medium is allowed to ferment in a 165-liter stirred fermentation tank for 3 to 5 days at a temperature of 30° C. Low air flow (0.12–0.25 v/v/m) and moderate rpm (200–250) in the stirred vessel maintain a dissolved oxygen level above 30% of air saturation.

EXAMPLE 2

Isolation of A42125

Whole fermentation broth (92 L) containing 3% Hyflo Supercel was filtered through a filter press. The broth filtrate (74 L) was adjusted to pH 7 with NaOH. Diaion HP-20 resin (9.4 L) was added. The mixture was stirred for 45 minutes and filtered. The filtrate was discarded, and the resin was washed three times with water (10 L each) and three times with acetonitrile:water (3:17, 10 L each) by resuspending, stirring and filtering. The washes were discarded. A42125 was eluted by suspending the resin in acetonitrile:water (1:1, 10 L) and stirring and filtering. Four successive elutions were performed, and each eluate fraction was assayed, using a *Micrococcus luteus* disc-plate assay. The first two eluants were combined, concentrated in vacuo to remove the acetonitrile and freeze dried to yield 94.9 g of crude A42125. The third eluant yielded 20.8 g of crude A42125.

EXAMPLE 3

Purification and Crystallization of A42125

The crude A42125 preparations obtained in Example 2 were combined (115.2 g) and dissolved in water (3 L). The solution was filtered to remove a precipitate, and the filtrate was applied to a column containing 3 L of Dowex 50×2 ($NH_4^+$), 100–200 mesh resin. The column was washed successively with 5 column volumes of water and 0.1 N $NH_4OH$. The fractions from the 2N $NH_4OH$ elution containing the largest amounts of A42125 were combined and concentrated to a volume of about 3 L. A42125 precipitated and was separated by filtration. The precipitate was dissolved in methanol (300 mL), and this solution was added to ether (6 L) to precipitate the A42125. This precipitate was filtered and dried to yield 16.6 g of A42125 as an amorphous powder. A second precipitate was obtained by further concentrating the aqueous solution and treating it in the same manner to yield 20.7 g of less pure A42125.

The first A42125 obtained (16.6 g) was dissolved in warm water (800 mL). This solution was allowed to stand overnight at room temperature, and A42125 crystallized. The crystals were separated by filtration and dried in vacuo to yield 10.6 g and 2.3 g (second crop) of crystalline A42125 (mp 149°–150° C.).

EXAMPLE 4

A42125-Enhanced Cattle Ration

A balanced, high-grain ration adapted to finish cattle is prepared by the following recipe:

| Ingredient | Percent | lbs/ton |
| --- | --- | --- |
| Corn, yellow | 50.25 | 1005.0 |
| Cobs, corn | 34.927 | 698.54 |
| Alfalfa meal, dehydrated, 17% | 4.00 | 80.0 |
| Soybean oil meal, solvent extracted | 4.00 | 80.0 |
| Urea, feed grade | 0.35 | 7.0 |
| Molasses, cane | 5.00 | 100.0 |
| Dicalcium phosphate | 0.65 | 13.0 |
| Salt | 0.35 | 7.0 |
| Calcium carbonate | 0.30 | 6.0 |
| Trace mineral premix[1] | 0.03 | 0.6 |
| Vitamin A + D3 Premix[2] | 0.07 | 1.4 |
| Vitamin E Premix[3] | 0.07 | 1.4 |
| A42125 | 0.003 | 0.06 |
| | 100.00 | 2000.0 |

[1]Trace mineral premix contains: 2.50% manganese as manganous oxide, 0.07% iodine as potassium iodide, 0.30% cobalt as cobalt carbonate, 0.50% copper as copper oxide, and 20.00% zinc as zinc sulfate
[2]Each pound of Vitamin A and D3 premix contains 2,000,000 USP Units Vitamin A and 225,750 USP Units Vitamin D3
[3]Each pound of Vitamin E premix contains 20,000 IU Vitamin E

We claim:
1. Antibiotic A42125, which has the following characteristics:
   State: White crystals (from water)
   m.p.: 149°–150° C.
   UV: No absorption
   IR (Kbr): Shown in the accompanying drawing;
   Titration (80% aqueous dimethylformamide): pKa's 5.2, 8.7 and 10.5
   Molecular weight: 2032 (field desorption mass spectrometry)
   Empirical formula: $C_{101}H_{184}N_2O_{38}$
   Amino acids: None found
   Solubility: Soluble in water or an alkali-metal, alkaline-earth metal, amine or acid addition salt of A42125.

2. A compound of claim 1 which is A42125 or a pharmaceutically acceptable salt of A42125.

3. A process for producing antibiotic A42125 of claim 1 which comprises cultivating *Nocardia aerocolonigenes* NRRL 18049, or an A42125-producing mutant thereof, in a culture medium containing assimilable sources of carbon, nitrogen, and inorganic salts under submerged aerobic fermentation conditions until substantial antibiotic A42125 activity is produced.

4. The process of claim 3 which includes the additional step of separating A42125 from the culture medium.

5. The process of claim 4 wherein *N. aerocolonigenes* NRRL 18049 is used.

6. A feed composition comprising animal feed and an amount of a compound of claim 2 which is effective for increasing feed utilization efficiency in ruminant animals.

7. A process for increasing feed-utilization efficiency in ruminant animals which comprises orally administering to the animal an effective propionate-increasing amount of a composition of claim 6.

* * * * *